US009675640B2

(12) United States Patent
Cheng et al.

(10) Patent No.: US 9,675,640 B2
(45) Date of Patent: Jun. 13, 2017

(54) MAGNETIC CALCIUM PHOSPHATE NANOPARTICLES, APPLICATIONS AND METHODS OF PREPARATION THEREOF

(75) Inventors: Xingguo Cheng, San Antonio, TX (US); Qingwen Ni, San Antonio, TX (US); Thomas B. Potter, Sugar Land, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 0 days.

(21) Appl. No.: 13/568,644

(22) Filed: Aug. 7, 2012

(65) Prior Publication Data

US 2014/0044643 A1    Feb. 13, 2014

(51) Int. Cl.
*A61K 33/42* (2006.01)
*A61K 49/18* (2006.01)
*A61N 1/40* (2006.01)
*B82Y 5/00* (2011.01)

(52) U.S. Cl.
CPC .......... *A61K 33/42* (2013.01); *A61K 49/1818* (2013.01); *A61N 1/403* (2013.01); *B82Y 5/00* (2013.01)

(58) Field of Classification Search
CPC .. A61K 41/00; A61K 49/183; A61K 47/4893; A61K 33/42; A61K 47/48861
See application file for complete search history.

(56) References Cited

U.S. PATENT DOCUMENTS

| | | | | |
|---|---|---|---|---|
| 4,728,570 | A * | 3/1988 | Ashman et al. | 428/327 |
| 5,783,217 | A * | 7/1998 | Lee et al. | 424/602 |
| 6,599,498 | B1 * | 7/2003 | Groman et al. | 424/9.34 |
| 7,259,210 | B2 | 8/2007 | Puckett, Jr. et al. | |
| 7,354,995 | B2 | 4/2008 | Imamura et al. | |
| 7,632,353 | B2 | 12/2009 | Hatono et al. | |
| 7,678,174 | B2 | 3/2010 | Tokuoka et al. | |
| 7,976,547 | B2 | 7/2011 | Vendrely et al. | |
| 8,153,255 | B2 | 4/2012 | Furuzono et al. | |
| 8,784,384 | B2 | 7/2014 | Boyden et al. | |
| 2001/0008649 | A1 * | 7/2001 | Layrolle | A61F 2/30767 427/2.24 |
| 2004/0220672 | A1 | 11/2004 | Shadduck | |
| 2008/0206296 | A1 | 8/2008 | Bouler et al. | |
| 2008/0319247 | A1 | 12/2008 | Forbes et al. | |
| 2009/0221730 | A1 | 9/2009 | Kowalski et al. | |
| 2010/0092364 | A1 | 4/2010 | Kasinath et al. | |
| 2010/0303722 | A1 | 12/2010 | Jin et al. | |
| 2011/0014296 | A1 | 1/2011 | Chen et al. | |
| 2011/0098374 | A1 | 4/2011 | Wichlas et al. | |
| 2011/0135577 | A1 | 6/2011 | Wu et al. | |
| 2013/0150267 | A1 | 6/2013 | Roddy | |
| 2013/0210960 | A1 | 8/2013 | Lee et al. | |
| 2015/0142112 | A1 | 5/2015 | Cheng et al. | |

OTHER PUBLICATIONS

Li, Z., et al., "Preparation and in vitro investigation of chitosan/nano-hydroxyapatite composite used as bone substitute materials", 2005, J. Mater. Sci., pp. 213-219.*
Hou, C., et al., "The fabrication and characterization of dicalcium phosphate dihydrate-modified magnetic nanoparticles and their performance in hyperthermia processes in vitro", 2009, Biomaterials, pp. 1-8.*
Pinto, H.P., et al., "First-Principles Studies of Paramagnetic Vivianite Fe3(PO4)2•8H2O Surfaces", J Phy Chem. C., 2014, pp. 6110-6121.*
Wu, H., et al., "Novel Magnetic Hydroxyapatite Nanoparticles as Non-viral Vectors for the Glial Cell Line-Derived Neurotrophic Factor Gene", Adv. Funct. Mater., 2010, pp. 67-77.*
Tampieri, A., et al., "Intrinsic magnetism and hyperthermia in bioactive Fe-doped hydroxyapatite", Acta Biomaterialia, Sep. 29, 2011, pp. 834-851.*
Wang, J., et al., "Preparation and Characterization of Chitosan-Coated Hydroxyapatite Nanoparticles as a Promising Non-V iral Vector for Gene Delivery", J. Applied Polymer Sci., 2011, pp. 3531-3540.*
Alexiou, Christoph et al., "Cancer Therapy With Drug Loaded Magnetic Nanoparticles-magnetic Drug Targeting", Journal of Magnetism and Magnetic Materials 323 (2011) 1404-1407, 2011, 1404-1407.
Denardo, Sally J. et al., "Thermal Dosimetry Predictive of Efficancy of 111 In—ChL6 Nanoparticle AMF-Induced Thermoablative Therapy for Human Breast Cancer in Mice", The Journal of Nuclear Medicine, vol. 48, No. 3, Mar. 2007, Mar. 2007, 437-444.
Farokhzad, Omid C. et al., "Targeted Nanoparticle-Aptamer Bioconjugates for Cancer Chemotherapy In Vivo", Proceedings of The National Academy of Sciences of the United States of America; VI. 103, No. 16, Apr. 18, 2006, 6315-6320, 2006, 6315-6320.
Galanzha, Ekaterina I. et al., "In Vivo Magnetic Enrichment and Multiplex Photoacoustic Detection of Circulating Tumour Cells", Nature Nanotechnology; vol. 4, Published online Nov. 15, 2009; DOI: 10.1038/NNANO.2009.333, Dec. 2009, 855-860.
Hou, Chun-Han et al., "The in Vivo Performance of Biomagnetic Hydroxyapatite Nanoparticles in Cancer Hyperthermia Therapy", Biomaterials, vol. 30, 2009, pp. 3956-3960, 2009, 3956-3960.
Kumar, R. et al., "Chitosan-mediated Crystallization and Assembly of Hydroxyapatite Nanoparticles Into Hybrid Nanostructured Films", Journal of the royal Society Interface, Apr. 2008, vol. 5, No. 21 pp. 427-439; downloaded Jul. 27, 2012 from http://rsif.royalsocietypublishing.org/content/5/21/427, 2008, Abstract only.

(Continued)

*Primary Examiner* — Michael G Hartley
*Assistant Examiner* — Lance Rider
(74) *Attorney, Agent, or Firm* — Grossman, Tucker et al.

(57) ABSTRACT

Magnetic calcium phosphate particles are provided including particles comprising iron oxide and calcium phosphate. A chitosan coating is present on the particles, wherein the particles are less than or equal to 1,000 nm, are magnetic and exhibit a positive charge in the range of 1 mVolts to 60 mVolts. The particles are provided by preparing a calcium hydroxide solution and filtering the calcium hydroxide solution in a membrane filter. An iron chloride solution is formed and combined with the filtered calcium hydroxide solution. In addition, the phosphoric acid solution is combined with the combined solutions of iron chloride and calcium hydroxide, forming a mixture including particles comprising iron oxide and calcium phosphate.

10 Claims, 14 Drawing Sheets

(56) References Cited

OTHER PUBLICATIONS

Mohapatra, M. et al., "Synthesis and Applications of Nano-Structured Iron Oxides/Hydroxides—A Review", International Journal of Engineering, Science and Technology; vol. 2, No. 8, 2010, 2010, 127-146.
Pareta, Rajesh A. et al., "Increased Osteoblast Density in the Presence of Novel Calcium Phosphate Coated Magnetic Nanoparticles", IOPScience; Nanotechnology 19 (2008) 265101 (7 pgs), 2008, 1-7.
Prakash, K. H. et al., "Wet-chemical Synthesis and Magnetic Property Studies of Fe(III) Ion Substituted Hydroxyapatite", MCB Molecular and Cellular Biomechanics, vol. 3, No. 4, pp. 177-178, 2006, 2006, 177-178.
Salvador-Morales, Carolina et al., "Multifunctional Nanoparticles for Prostate Cancer Therapy", Expert Review of Anticancer Therapy 9[2], 211-221 2009, Corrigendum Correction Notice 9.11 (Nov. 2009); p. 1698, 2009, 211-221.
Tran, Nhiem et al., "Effects of Magnetite and Maghemite Nanoparticles on Bone Cell and *Staphylococcus aureus* Functions", ingentaconnect, Technology & Innovation, vol. 13, No. 1, 2011, pp. 39-50;, downloaded Jul. 26, 2012 from http://www.ingentaconnect.com/content/cog/ti/2011/00000013/00000001/art00004, 2011, Abstract only.
Tran, Nhiem et al., "Iron Oxide Nanoparticles: Novel Drug Delivery Materials for Treating Bone Diseases", Advanced Materials Research, vol. 89-91, 411, Thermec 2009 Supplement, downloaded on Jul. 26, 2012 from http://www.scientific.net/AMR.89-91.411, 2009, Abstract only.
Wang, Andrew Z. et al., "Superparamagnetic Iron Oxide Nanoparticle-Aptamer Bioconjugates for Combined Prostate Cancer Imaging and Therapy", ChemMedChem 2008; vol. 3, pp. 1311-1315, 2008, 1311-1315.
Wu, Hsi-Chin et al., "A Novel Biomagnetic Nanoparticle Based on Hydroxyapatite", IOPScience, Nanotechnology, 2007, vol. 18, No. 16; Abstract only downloaded on Jul. 26, 2012 from http://iopscience.iop.org/0957-4484/18/16/165601/, 2007, Abstract only.
Zhang, Yan et al., "Magnetic Hydroxyapatite-Encapsulated y-Fe2O3 Nanoparticles Functionalized With Basic Ionic Liquids for Awueous Knoevenagel Condensation", Applied Catalysis A: General 366 (2009) pp. 141-147, Dec. 2009, 141-147.
Wu, Hsi-Chin, et al, "A Novel Biomagnetic Nanoparticle Based on Hydroxyapatite", Nanotechnology 18 (2007) 165601 (9 pgs) [doi:10.1088/0957-4484/18/16/165601].
Damico, Dennis J., "Reactive Acrylic Adhesives", 2003 Taylor & Francis Group, LLC (38), 13 pgs.
Harris, Craig A, et al., "Metal Artifact Reduction in Musculoskeletal Magnetic Resonance Imaging", Orthopedic Clinics of North America, 2006; 37; pp. 349-359.
Kawashita, M., et al. "PMMA-based Bone Cements Containing Magnetite Particles for the Hyperthermia of Cancer"; Acta Biomaterialia 6 (2010): pp. 3187-3192.
Kusaka, M, et al, "Effect of hyperthermia by magnetite cement on tumor-induced bone destruction"; Journal of Orthopaedic Science. 2002; 7(3): pp. 354-357.
Li, Z, et al, "In vitro assessment of poly(methylmethacrylate)-based bone cement containing magnetite nanoparticles for hyperthermia treatment of bone tumor"; Journal of Biomedical Materials Research—Part A. 2012;100 A(10): pp. 2537-2545.
Mathieu, JB, et al, "Preliminary investigation of the feasibility of magnetic propulsion for future microdevices in blood vessels"; Bio-Medical Materials and Engineering. 2005;15(5): pp. 367-374.
Mohamed, M., et al, "In situ forming implants for local chemotherapy and hyperthermia of bone tumors"; Journal of Drug Delivery Science and Technology. 2012; 22 (5): pp. 393-408.
Ohura, K., et al. "A heat-generating bioactive glass-ceramic for hyperthermia."; Journal of Applied Biomaterials; 1991; 2(3): pp. 153-159.
Portela, A, et al, "An in vitro and in vivo investigation of the biological behavior of a ferrimagnetic cement for highly focalized thermotherapy"; Journal of Materials Science: Materials in Medicine. 2010;21(8): pp. 2413-2423.
Portela, A, et al. "Highly focalised thermotherapy using a ferrimagnetic cement in the treatment of a melanoma mouse model by low temperature hyperthermia"; International Journal of Hyperthermia. Mar. 2013; 29(2):121-132.
Powell, J., et al, "Numerical simulation of SAR induced around Co—Cr—Mo hip prostheses in situ exposed to RF fields associated with 1.5 and 3 T MRI body coils"; Magnetic Resonance in Medicine. 2012; 68(3): pp. 960-968.
Takegami, K., et al. "New ferromagnetic bone cement for local hyperthermia"; Journal of Biomedical Materials Research. 1998; 43(2): pp. 210-214.
Tang, Z, et al., "Preparation and characterization of PMMA-based cements containing magnetic nanoparticles for the magnetic hyperthermia"; Advanced Materials Research, vol. 647 2013. pp. 155-159.
Kuhn, K.-D., "Bone Cements, Up-to-Date Comparison of Physical and Chemical Properties of Commercial Materials" Springer-Verlag Publication, 2000, pp. 246-247.
Minyuk, P.S. et al, "High-temperature Thermomagnetic Properties of Vivianite Nodules, Lake El'gygytgyn, Northeast Russia", Climate of the Past, 9, pp. 433-445, 2013 [doi: 10.5194/cp-9-433-2013].
Tien, Pei-Lin, et al, Thermal and X-Ray Studies on Earthy Vivianite in Graneros Shale (Upper Cretaceous), Kansas; The American Mineralogist, vol. 54, Sep.-Oct. 1969, pp. 1355-1362.
U.S. Office Action, mail date Apr. 20, 2016 issued in U.S. Appl. No. 14/083,215 (10 pgs.).
Notice of Allowance, mail date Oct. 5, 2016 issued in U.S. Appl. No. 14/083,215 (5 pgs).

* cited by examiner

MAGNETIC CALCIUM PHOSPHATE NANOPARTICLES, APPLICATIONS AND METHODS OF PREPARATION THEREOF

FIELD OF INVENTION

The present disclosure relates to magnetic calcium phosphate nanoparticles, applications for use of such particles and methods of preparing such particles.

BACKGROUND

Superparamagnetic iron oxide nanoparticles have been explored for uses in various medical applications, including, for example, MRI, hyperthermia therapy, and drug release systems. In MRI applications, superparamagnetic iron oxide nanoparticles have been investigated as contract agents and breast tumor imaging. In one study, nanoparticles that were modified with tumor targeting ligands (e.g., breast cancer cell surface receptor urokinase-type plasminogen activator) accumulated in mice breast tumors and generated strong contrast for imaging by clinical MRI (3 Tesla). In another study, targeted nanoparticles were used to detect circulating breast cancer cells in the blood, again using a mouse model.

In hyperthermia therapy, under median-level alternating magnetic field (AMF), magnetic nanoparticles can generate heat to induce breast cancer cell apoptosis. In one study, thermoablative therapy of breast cancer in mice was performed using antibody (mAb)-linked iron oxide nanoparticles. The magnetic nanoparticles were injected intravenously. The nanoparticles targeted human breast cancer xenografts in the mice, resulting in a delay in tumor growth after the AMF was applied.

Magnetic field drug release delivery systems have been investigated in the form of iron oxide loaded gels (e.g., gelatin, PVA), scaffolds, microbeads, composite membranes, nanoemulsions, silica nanocapsules or polymer nanoparticles. In one study, magnetic nanoparticles were bound with a chemotherapy drug and tested for targeted chemotherapy in a rabbit liver tumor model. Magnetic particles have also been investigated for both imaging and drug delivery in prostate cancer.

There is concern that pure iron oxide leads to acute toxicity. Further, due to anisotropic bipolar attraction, iron oxide nanoparticles may aggregate. The nanoparticles systems described above are based on encapsulated iron oxide nanoparticles to combat or mitigate aggregation and toxicity. The nanoparticles and any associated drug may be dispersed in oil/water and encapsulated by a multilayer polymer/liposome shell. However, heat conduction is relatively difficult with the multilayer shell as heat generated by the iron oxide must be transferred through the relatively low conductivity water/oil phase and then transferred to and through the polymer shell.

Accordingly room for improvement remains in the field of iron oxide nanoparticle formation and use, wherein the iron oxide particles may be more biocompatible, yet still transmit heat into surrounding matter.

SUMMARY

An aspect of the present disclosure relates to a method of forming magnetic calcium phosphate particles. The method may include preparing a calcium hydroxide solution and filtering the calcium hydroxide solution through a filter. The method may also include forming an iron chloride solution and combining the iron chloride solution with the filtered calcium hydroxide solution. In addition, the method may include combining a phosphoric acid solution (without or with chitosan) with the combined solutions of iron chloride and calcium hydroxide and forming a mixture including particles comprising iron oxide and calcium phosphate.

Another aspect of the present disclosure relates to a preparation of magnetic calcium phosphate particles. The particles comprise iron oxide and calcium phosphate. Furthermore, a polysaccharide coating such as chitosan may be present on the particles. The particles are less than or equal to 1,000 nm, are magnetic, and exhibit a positive charge in the range of 1mVolts to 60 mVolts.

A further aspect of the present disclosure relates to a method of treating a disease, condition or associative disorder including administering an effective amount of magnetic calcium phosphate particles to a patient/animal. And yet a further aspect of the present disclosure relates to a method of combining a sample including the biological composition with magnetic calcium phosphate particles, wherein the magnetic calcium phosphate particles bind with the biological composition; and analyzing the biological composition.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

The present disclosure relates to magnetic calcium phosphate solid nanoparticles and or microparticles as well as a method of producing such particles and applications for such particles. The iron oxide/calcium phosphate particles may be used in applications where iron oxide and calcium phosphate are independently utilized. The magnetic calcium phosphate particles also combine the magnetic properties of iron oxide and protein/drug adsorption capabilities of the calcium phosphate. Applications of the particles may include, for example, tumor hyperthermia therapy, thermal drug delivery, targeting, imaging contrast agent, disease detection, bio-separation, bone repair, etc.

The magnetic calcium phosphate particles are preferably formed by co-precipitation of iron oxide and calcium phosphate into particles. The particles may also include a linear polysaccharide (carbohydrate molecules of repeated monomer units joined by glycosidic bonds) such as a chitosan coating which may provide a relatively stable colloid, i.e., having little agglomeration. The particles are relatively low cost and relatively easy to co-precipitate. In addition, the particles are relatively more biocompatible. The iron oxide is included in the crystal lattice (intracrystalline and intercrystalline) and it may not be easily removed under physiological conditions. In addition, calcium phosphate is a natural component of human bone and it is a generally recognized as safe material (GRAS). Accordingly, the magnetic calcium phosphate particle is relatively more biocompatible than iron oxide alone.

Figure 1:
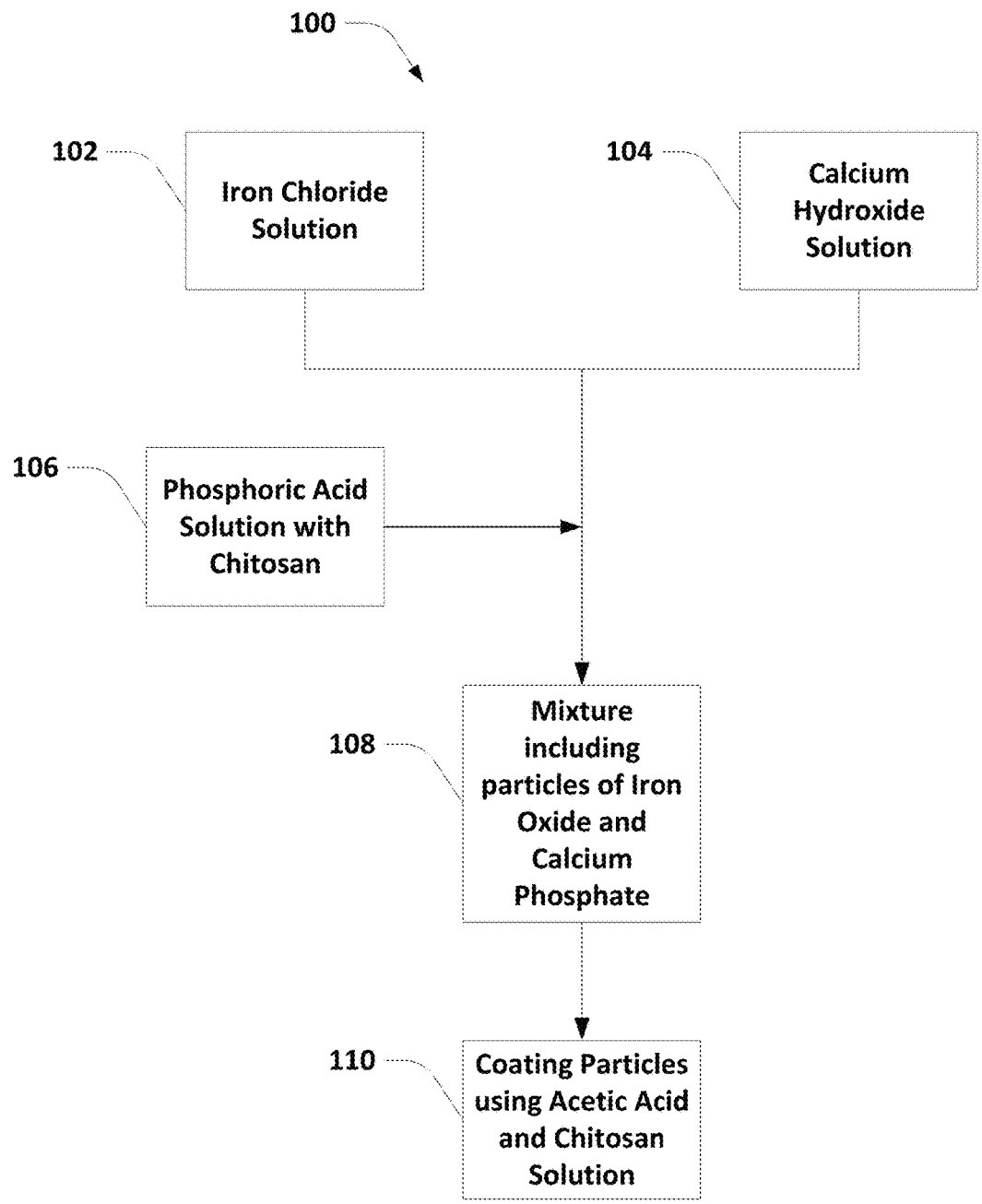
FIG. 1 illustrates a general method of preparing magnetic calcium phosphate nanoparticles.

FIG. 1 illustrates a general method 100 of producing the iron oxide/calcium phosphate particles includes or consists essentially of or consists of combining solutions of iron chloride 102 and calcium hydroxide 104 and adding an inorganic acid such as phosphoric acid 106 to precipitate particles 108 in a mixture, wherein the particles include iron oxide and calcium phosphate. The phosphoric acid may contain chitosan as illustrated or chitosan may not be present in this step. After, the particles are added to a chitosan and acetic acid solution coating the particles with chitosan 110.

Figure 2:
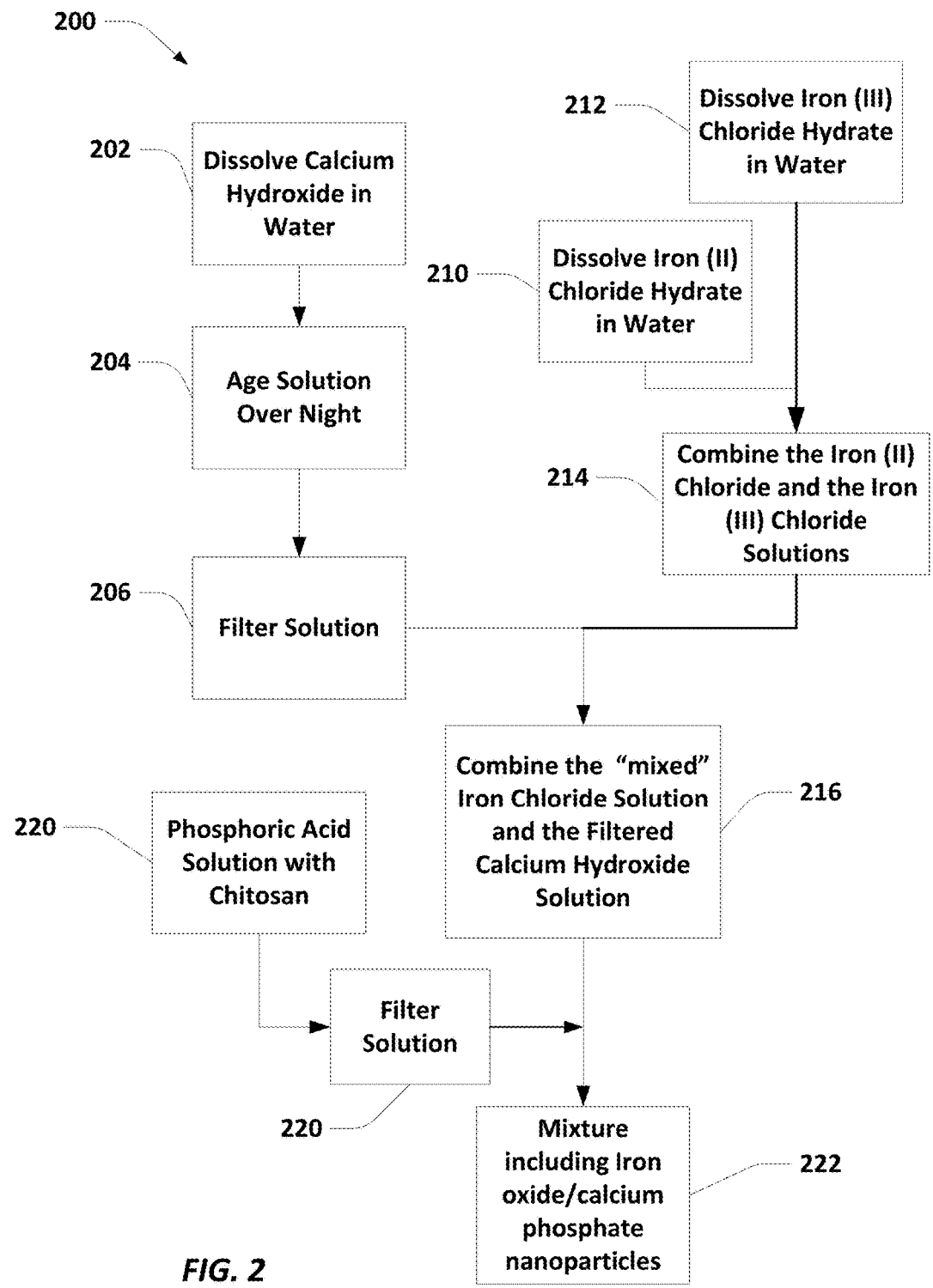
FIG. 2 illustrates a method of preparing magnetic calcium phosphate nanoparticles from solutions of calcium hydroxide, iron (II) chloride, iron (III) chloride, and phosphoric acid and chitosan.

FIG. 2 illustrates the preparation 200 of the combined solutions of the calcium hydroxide solution and the iron chloride solution. The calcium hydroxide solution is prepared by stirring and dissolving calcium hydroxide (Ca(OH)$_2$) in the water 202. The water herein may include, for example, deionized water or nanopure grade water having a resistivity of >18 MΩ/cm$^2$. The calcium hydroxide may be provided at a concentration of 0.001 to 48% by weight (% wt.), relative to the total weight of the solution, including all values and increments therein, such as 2.5% by wt.

The solution may be allowed to age overnight (e.g. between 8 to 24 hours, including all values and increments therein) 204 without agitation. Then the calcium hydroxide solution may be passed through a filter membrane 206 preferably having a porosity of 0.45 μm or less, including all values and increments therein, such as from 100 nm to 450 nm. Particles of calcium hydroxide larger than 0.45 μm are removed from the solution. Removal of larger calcium hydroxide particles may prevent the formation of magnetic calcium phosphate particles that are greater than a desired size, i.e., greater than 1 μm. Accordingly, filtration is considered to be preferable to the process herein of forming the magnetic calcium phosphate particles. After filtration, the concentration of the calcium hydroxide solution may then be measured and verified by stirring the solution well and measuring the density of the solution.

The iron chloride solution may be prepared from two separate iron chloride solutions, a solution of iron (II) chloride and a solution of iron (III) chloride. Specifically, a solution of iron (II) chloride is prepared by dissolving iron (II) chloride hydrate (FeCl$_2$.4H$_2$O) in water 210. Similarly, a solution of iron (III) chloride is prepared by dissolving iron (III) chloride hydrate (FeCl$_3$.6H$_2$O) 212.

The concentration of the iron (II) chloride is preferably provided at a mol ratio of 1 mol iron (II) chloride hydrate to 10 mol of calcium hydroxide, based on the measured concentration of the calcium hydroxide after filtration. While calcium hydroxide may therefore be preferably in molar excess to the iron (II) chloride, other molar ratios are contemplated. For example, one may utilize molar ratios of iron (II) chloride to calcium hydroxide of 1:1 to 1:20.

The concentration of the iron (III) chloride is also preferably provided at a mol ratio of 1 mol iron (III) chloride hydrate to 10 mol of calcium hydroxide, based on the measured concentration of the calcium hydroxide after filtration. While calcium hydroxide may therefore preferably be in molar excess to the iron (III) chloride, other molar ratios are contemplated. For example, one may utilize molar ratios of iron (III) chloride to calcium hydroxide of 1:10 to 10:1. The iron (II) chloride solution and iron (III) chloride solution are then combined to obtain a "mixed" iron chloride solution 214, "mixed" meaning a solution containing both species of iron chloride, i.e., iron (II) chloride and iron (III) chloride.

The calcium hydroxide solution and the "mixed" iron chloride solution are then combined and stirred until homogenous 216. The pH of the combined solutions may be in the range of 7 to 12.6, including all values and increments therein, such as a pH of 11.5. The solution may also be dark brown-black in color. The combined calcium hydroxide and "mixed" iron chloride solutions may be brought to a temperature in the range of 30° C. to 100° C., including all values and increments therein and preferably from 35° C. to 45° C. or 40° C., by heating in a water bath while stirring. One may also heat the calcium hydroxide solution to a temperature in the range of 30° C. to 100° C., including all values and increments therein and preferably in the range of 35° C. to 45° C. or 40° C., in a water bath prior to the addition of the "mixed" iron chloride solution to the calcium hydroxide solution.

An inorganic acid, such as a phosphoric acid solution may then be prepared by dissolving phosphoric acid in water 218. The phosphoric acid solution may have a concentration in the range of 1 to 50% weight/volume (% w/v), including all values and increments therein. A polysaccharide such as chitosan is optionally included in the phosphoric acid solution at a concentration of 0.01 to 10.0% by weight/volume (w/v), including all values and increments therein and preferably at 0.5% w/v to 1.5% w/v or 1% w/v, prior to titration with the phosphoric acid solution, as illustrated in FIG. 2.

The phosphoric acid/chitosan solution is also filtered 220. Filtration is accomplished using a first filter having a first pore size in the range of 5 μm or less, such as 5 μm to 0.5 μm, including all values and increments therein. The first filtration is then followed by a second filtration using a second filter having a pore size of 0.45 μm or less, such as 100 nm to 450 nm, including all values and increments therein. Filtration may be facilitated using syringe filters or other filtration mechanisms.

The filtered phosphoric acid/chitosan solution may be added dropwise to the combined solutions of the "mixed" iron chlorides and the calcium hydroxide until a pH of 5 to 7, including all values and ranges therein and preferably 5.00, is obtained. The combination of these solutions forms a mixture of magnetic iron oxide calcium phosphate particles 222 which may include Fe$_2$O$_3$ and/or Fe$_3$O$_4$ and calcium phosphate Ca$_x$(PO$_4$)$_y$, wherein the ratio of x:y may be in the range of 1 to 3. The mixture, including the magnetic calcium phosphate particles, is aged overnight (i.e., 8 to 24 hours, including all values and increments therein) at room temperature, i.e., 21° C. to 25° C., including all values and increments therein.

Figure 3:
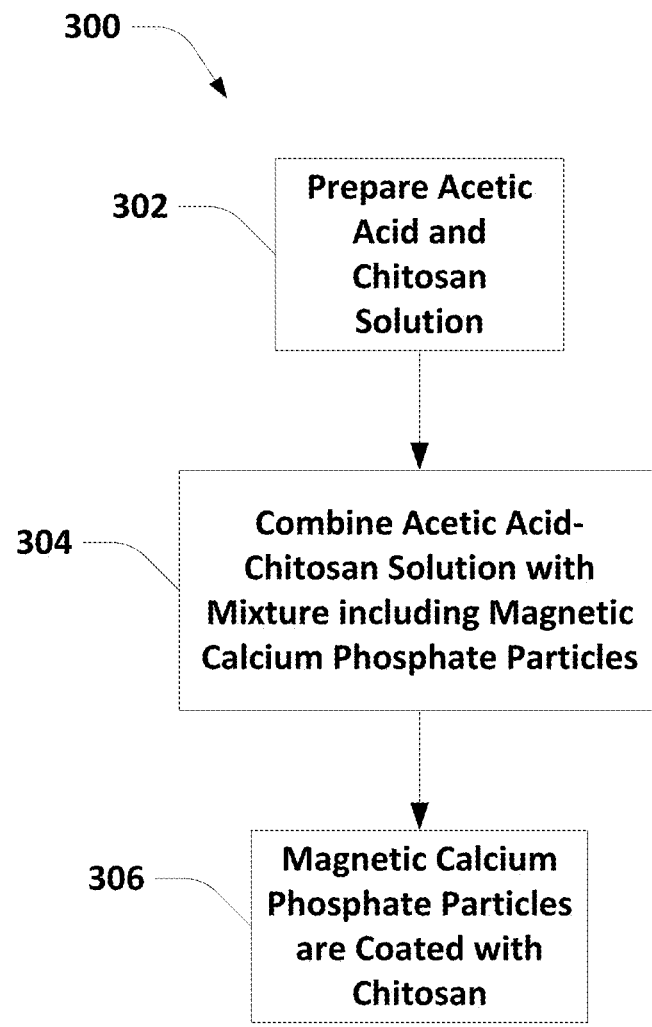
FIG. 3 illustrates a method of coating magnetic calcium phosphate nanoparticles with chitosan.

FIG. 3 illustrates a method of coating the magnetic calcium phosphate particles 300. The method includes preparing a solution of chitosan and an organic acid such as an aliphatic carboxylic acid, such as acetic acid 302, having a concentration of chitosan from 0.01 to 10 percent by weight in the total solution. The acetic acid may be provided at a concentration of 1% by w/v to glacial acetic acid including all values and increments therein, such as 1% by w/v.

The acetic acid/chitosan solution is combined with the mixture including the magnetic calcium phosphate particles 304. The acetic-acid solution and mixture is heated to a temperature of 100° C., or less, including all values and increments in the range of 21° C. to 100° C., such as preferably at 40° C., overnight (i.e., from 8 to 24 hours, including all values and increments therein). The acetic-acid solution and mixture is then removed from heat and aged overnight (i.e., from 8 to 24 hours, including all values and increments therein) while stirring. The solution is then sonicated or otherwise agitated, reducing the particle size, for a period of 10 minutes to 240 minutes, including all values and increments therein, such as 30 minutes. The magnetic calcium phosphate particles, including a chitosan coating, may then be washed and, optionally, lyophilized into dry powder, or used directly as a suspension.

The chitosan coating may provide free amine groups, allowing for surface modification of the particles. For example, the particles may be fixed to amino groups in peptides. Further, the chitosan provides an increase the smoothness of the particle surface and improves the particle water dispersity. Thus, the chitosan improves particle stability in aqueous liquids or ethanol, preventing agglomerations.

The resulting particles exhibit an effective diameter in the range of 10 nm to 100 μm, including all values and increments therein, and preferably in the range of 100 nm to 500 nm, more preferably 200 nm to 400 nm, etc. The effective diameter may be understood as mean diameter by cumulant analysis. The particles also exhibit a polydispersity in the range of 0.01 to 0.5, including all values and increments therein, such as 0.110 or 0.120. Further, the particles may exhibit a relatively high positive charge, i.e., zeta potential, in the range of 1 to 60 mVolts, including all values and increments therein, such as 50 mVolts. Such zeta potential is understood to indicate, for example, that the particles exhibit good stability in colloidal dispersions.

Figure 4A:
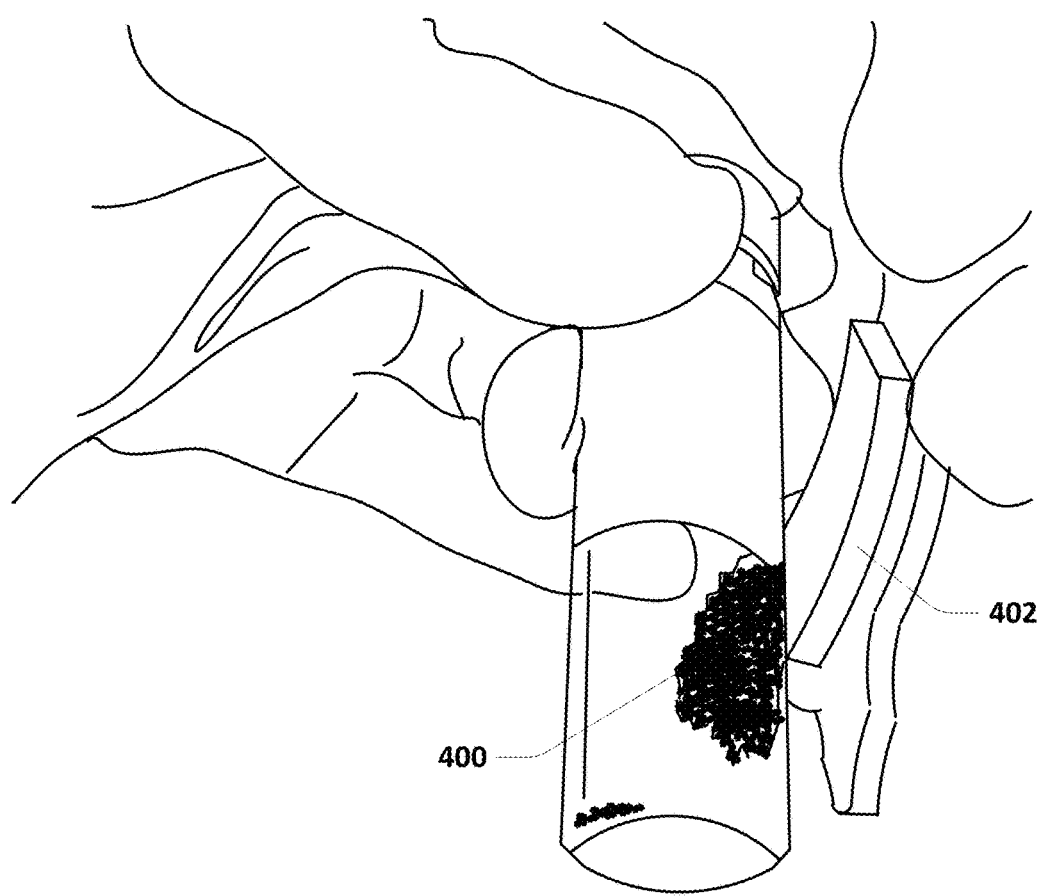
FIGS. 4a, 4b and 4c illustrate the relatively strong magnetism observed of the fabricated magnetic calcium phosphate nanoparticles, having the ability to move along with the magnets, be arrested by the magnets and be attracted to the surface of magnets.
Figure 4B:
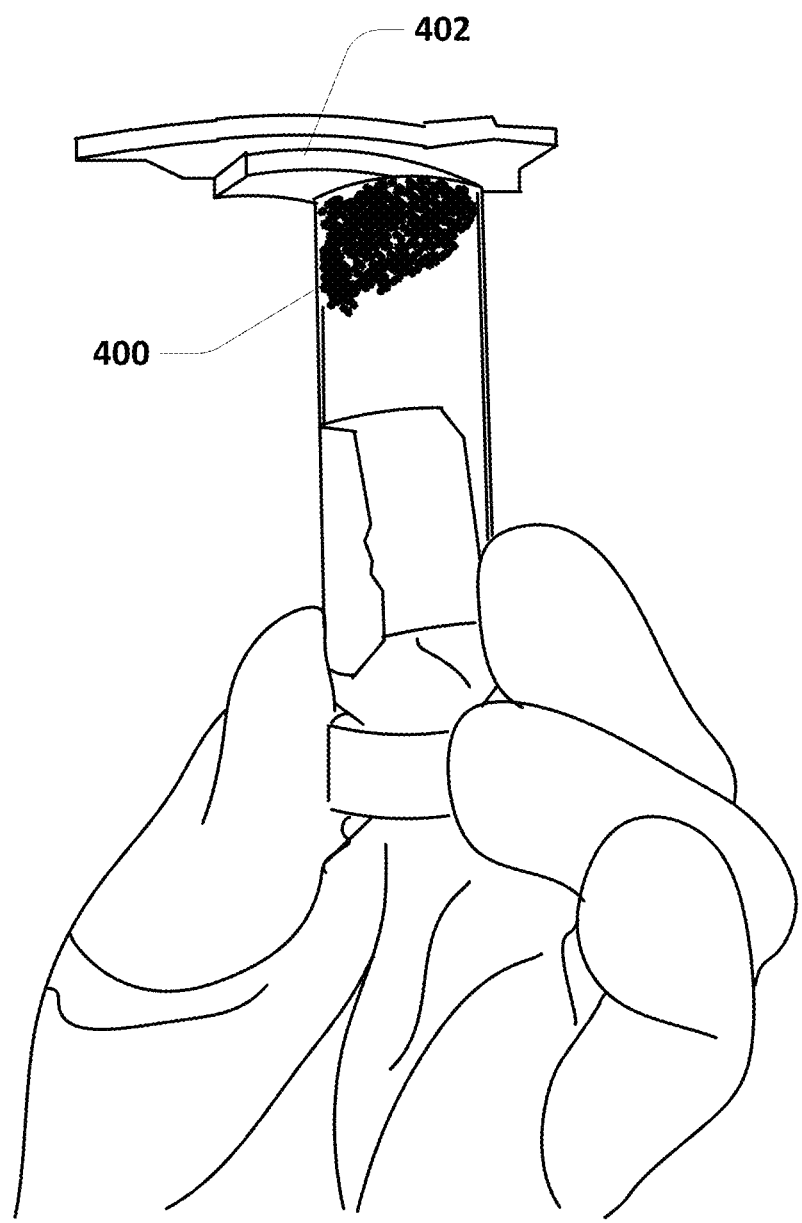
Figure 4C:
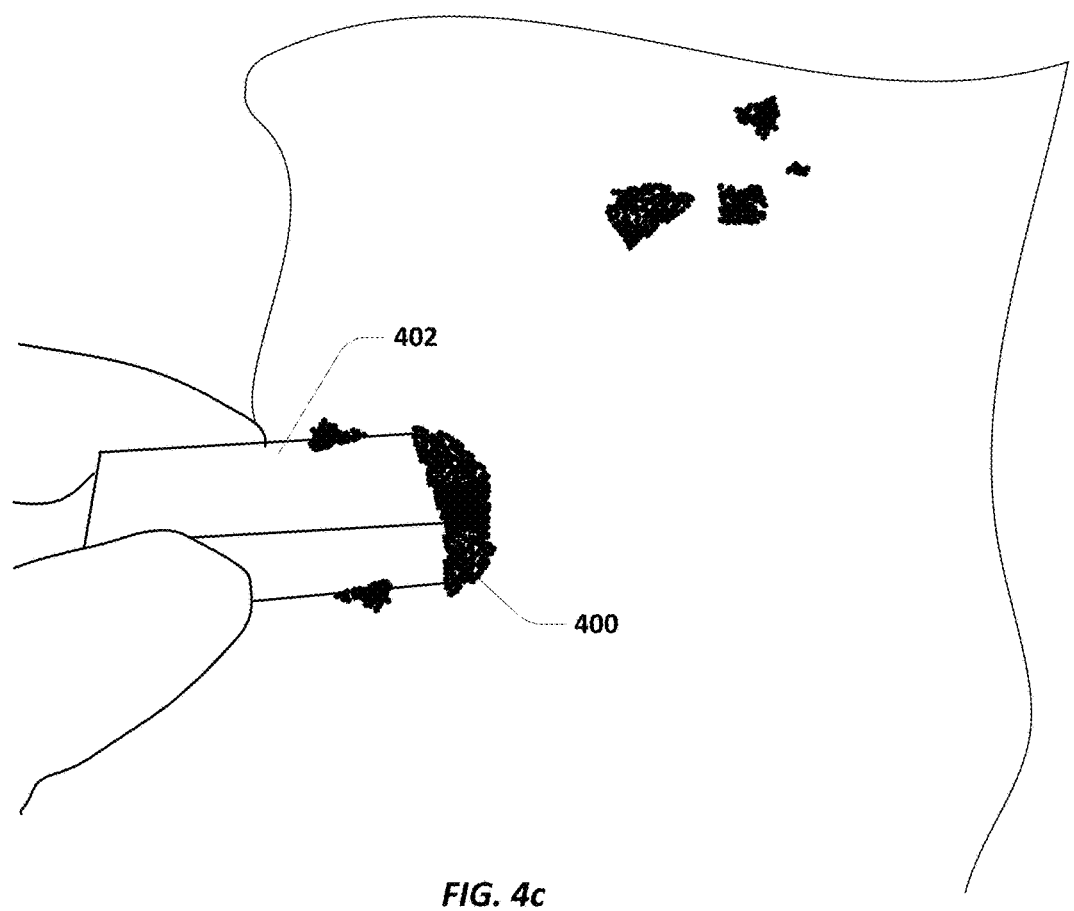

The magnetic calcium phosphate particles demonstrate a relatively strong magnetism. FIGS. 4a, 4b and 4c include illustrations of observed behavior of the magnetic calcium phosphate particles. The particles 400 move along with magnets 402, are arrested by magnets and/or are attracted to the surface of magnets. In these photos magnets have a flux density about 1.3 Tesla (T).

The magnetic calcium phosphate particles discussed herein may be utilized to treat, prevent or diagnose a particular disease or condition by administering the magnetic calcium phosphate particles to a subject. In various instances, the nanoparticles are administered alone or are included within a pharmaceutical formulation. The magnetic calcium phosphate particles may be incorporated into a variety of pharmaceutical formulations for the treatment of a disease, condition or an associative disorder in a patient. "Treatment" or "treating" is understood herein to identify, diagnose, detect, target, ameliorate, reduce, minimize or limit the extent of the disease, condition or associative disorder.

Additional pharmaceutical agents may be utilized in combination with the nanoparticles in the pharmaceutical composition. Such pharmaceutical agents may include one or more of the following: chemotherapy agents (such as e.g., Cisplatin), analgesics, antibiotics, antiseptics, reflux suppressants, antidopaminergics, proton pump inhibitors (PPI's), H2-receptor antagonists, cytoprotectants, prostaglandin analogues, opioids, beta-receptor blockers, calcium channel blockers, cardiac glycosides, antiarrhythmics, nitrate, antianginals, vasoconstrictors, vasodilators, peripheral activators, ACE inhibitors, angiotensin receptor blockers, alpha-blockers, anticoagulants, heparin, antiplatelet drugs, fibrinolytics, anti-hemophilic factors, haemostatic drugs, hypolipidaemic agents, statins, hypnotics, anaesthetics, antipsychotics, antidepressants, antiemetics, anticonvulsants/antiepileptics, anxiolytics, barbiturates, stimulants, benzodiazepines, cyclopyrrolones, dopamine antagonists, antihistamines, cholinergics, anticholinergics, cannabinoids, 5-HT (serotonin) antagonists, non-steroidal anti-inflammatory drugs, muscle relaxants, neuromuscular drugs anticholinesterases, adrenergic neurone blocker, sympathomimetics, parasympatholytics, mydriatics, cycloplegics, antifungals, corticosteroids, carbonic anhydrase inhibitors/hyperosmotics, miotics, parasympathomimetics, prostaglandin agonists/prostaglandin inhibitors, cerumenolyti bronchodilators, antitussives, mucolytics, decongestants, beta2-adrenergic agonists, androgens, antiandrogens, gonadotropin, human growth hormones, insulin, antidiabetics, thyroid hormones, antithyroid drugs, calcitonin, diphosphonate, vasopressin analogues, quinolones, vaccines, immunoglobulins, immunosuppressants, interferons, monoclonal antibodies, electrolytes, parental nutritional supplements, etc. Other pharmaceutical compositions may be included in addition to or apart from those mentioned above.

The phrases "pharmaceutical or pharmaceutically acceptable" are understood as molecular entities and compositions that do not produce an adverse, allergic or other untoward reaction when administered to a subject, such as, for example, a human. Stated another way, the composition may be generally safe, non-toxic, and neither biologically nor otherwise undesirable. It should be understood however, that aberrations are plausible, where a relatively statistically insignificant portion of the population may be adversely affected by a given composition. The preparation of a pharmaceutical composition is generally known to those of skill in the art. Moreover, for animal (e.g., human) administration, it is preferred that the preparations meet sterility, pyrogenicity, general safety, and purity standards as required by the FDA Office of Biological Standards.

An "effective amount" of a pharmaceutical formulation is, generally, defined as that amount sufficient to identify, diagnose, detect, target, ameliorate, reduce, minimize or limit the extent of the disease or condition. More or less rigorous definitions may apply, including elimination, eradication, or cure of a disease or condition. Less rigorous definitions may apply as well, including producing reproducible and evaluable images. As understood in the art, the effective amount of the magnetic calcium phosphate particles may vary based on the component, the nature and severity of the condition to be treated, the age and condition of the subject to be treated, and other factors.

A "pharmaceutically acceptable carrier" may be used to facilitate administration of the magnetic calcium phosphate particles parenterally, including for example, infusion, injection or implantation; or enterally, including for example pills, tablets, or suppository. "Pharmaceutically acceptable carriers" include any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

The actual dosage amount of a composition of the present invention administered to a subject can be determined by physical and physiological factors such as body weight, severity of condition, the type of disease being treated, previous or concurrent therapeutic interventions, idiopathy of the patient and the route of administration. The practitioner responsible for administration will, in any event, determine the concentration of active ingredient(s) in a composition and appropriate dose(s) for the individual subject.

Figure 5:
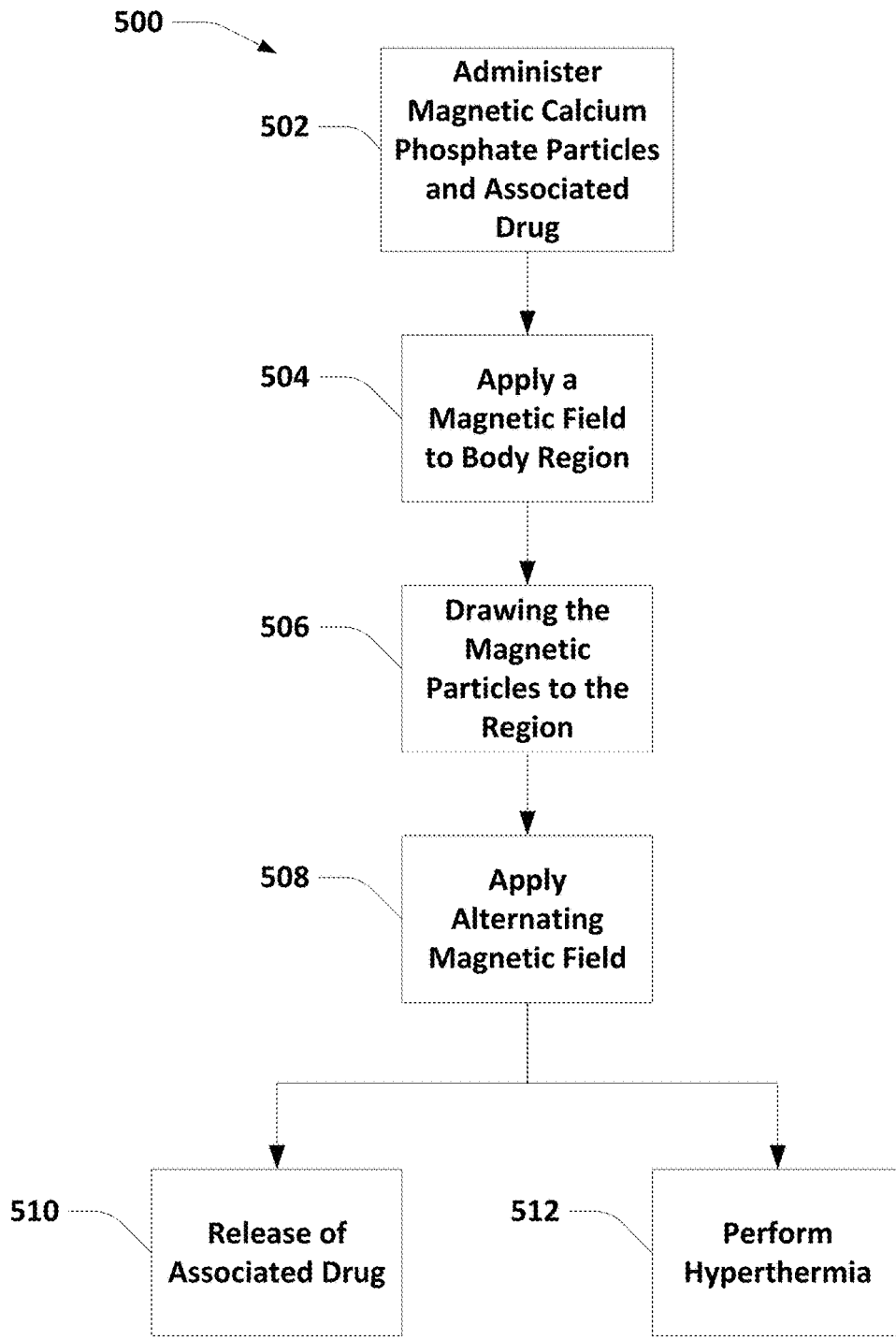
FIG. 5 illustrates a method of treatment by administering, targeting and heating magnetic calcium phosphate nanoparticles.

FIG. 5 illustrates the employment of the magnetic calcium phosphate nanoparticles described herein in a pharmaceutical formulation, which in this example may include a chemotherapy drug 500. The drug might be bound to magnetic calcium phosphate nanoparticles either physically (e.g., electrostatic interaction) or covalently. The magnetic calcium phosphate nanoparticles may be administered to a patient parenterally via intra-artery injection 502. Other routes of injection such as interperitoneal, intervenous, subcutaneous, or intratumoral, or inside a specific tissue are also possible. A permanent magnet may then be applied to a specific region of the patient's body 504, such as proximal to and within a tumor, as tumors require arteries to grow. The magnetic particles may then be drawn to the specific location by using a strong magnet 506. Thus, the magnetic calcium phosphate particles allow for magnetic targeting of the particles and the drug. In combining the particles with other drugs, such as the chemotherapy drugs, the chemotherapy drugs may be delivered to a very specific location of the body using the magnetic targeting, potentially reducing the overall toxic effects of the drugs.

The calcium phosphate particles also allow for triggered release of drugs and/or ablation of cells. Referring again to FIG. 5, an alternating magnetic field may be applied to heat up the particles within the tumors 508. The heated particles may then trigger or accelerate the release of the chemotherapy drug simultaneously 510. Release of the particles may also be assisted by tumor pH. Further, the heated particles may kill the cells associated with the tumors through hyperthermia 512 regardless of whether additional pharmaceutical compositions are presented with the particles.

In other embodiments, the carrier may include an injectable or implantable tissue scaffold, such as a bone cement-like scaffold or thermo-responsive polymer formulation such as Poly(N-isopropylacrylamide) (pNIPAM), in which the particles may be incorporated. The scaffold may be positioned within the patient's body. Again, an alternating magnetic field may then be applied to heat up the magnetic particles heating the surrounding scaffold composition and curing the scaffold composition. Heating of the particles may also release drug compositions, which may provide anti-rejection drugs, growth promoters, etc., into the locale of the scaffold. As calcium phosphate particles may be utilized in tissue scaffolds (including bone tissue scaffolds), one may beneficially substitute the magnetic calcium phosphate particles with particles already in use, providing the additional magnetic functionality described herein.

In combination with the above described embodiments, or independent therefrom, the magnetic calcium phosphate particles may be used as a contrast agent for imaging. In addition, the particles may be used as a label to identify specific biological compositions within the body for imaging purposes. Imaging methods may include, but are not limited to, MRI, CT scans, NIR, PET, and fluorescent imaging. For example, a cancer target ligand and near infrared (NIR) dye can both be conjugated to the surface of magnetic calcium phosphate nanoparticles. NPs will travel and bind with tumor cells or accumulate inside the solid tumor. NIR image station can be used to detect the tumor inside human or animal body.

The magnetic calcium phosphate particles may also be utilized as a label to identify biological compositions of interest in assays, which may include analytic procedures for qualitatively or quantitatively measuring the presence, amount or characteristics of a functional activity of a target entity or analyte. Examples of assays in which the magnetic calcium phosphate particles may be utilized in include flow cytometry, bio-separation, chromography, and various other separation and imaging methods. Magnetic calcium phosphate nanoparticles can be used for many other applications that pure calcium phosphate nanoparticles are used, e.g., drug delivery, gene delivery, adjuvants, vaccine, etc.

For example, the magnetic calcium phosphate particles may be utilized in a method of purification of biological compositions. Biological composition may include cells, compositions within cells, cell fragments, proteins, peptides, etc., to which the magnetic calcium phosphate particles may bind directly or indirectly through a ligand or other functional group. Specifically, the sample including the biological composition of interest may be combined with the magnetic calcium phosphate particles. The magnetic calcium phosphate particles may be functionalized with a group that specifically targets the biological compositions of interest.

In one example, the sample may then be passed through an adsorbent column, such as a liquid chromatography column, high performance liquid chromatography column, etc. The sample may then be eluted through the column, wherein the biological composition of interest may be separated from the sample. Various characteristics of the biological composition may then be analyzed. In another example, where the biological composition includes cells or cell fragments, the sample may be passed through a flow cytometer for analysis.

EXAMPLES

Example 1

Magnetic calcium phosphate nanoparticles were prepared as follows. A 250 mL 2.5% w/v solution of calcium hydroxide was prepared by stirring and dissolving calcium hydroxide in Nanopure water. The solution was allowed to settle overnight without agitation. The calcium hydroxide solution was passed through a filter membrane having a porosity of 0.45 μm. After filtration, the concentration of the calcium hydroxide solution was measured and verified by stirring the solution well and measuring the density of the solution.

Iron chloride solution was prepared by combining solutions of iron (II) chloride and iron (III) chloride. The iron (II) chloride solution was prepared by dissolving iron (II) chloride hydrate ($FeCl_2 \cdot 4H_2O$) in 1.25 ml of water at a mol ratio of 1 mol iron (II) chloride hydrate to 10 mol of calcium hydroxide, based on the measured concentration of the calcium hydroxide after filtration. A solution of iron (III) chloride was prepared by dissolving iron (III) chloride hydrate (FeCl$_3$.6H$_2$O) in 1.25 ml of water at a mol ratio of 1 mol iron (III) chloride hydrate to 10 mol of calcium hydroxide, based on the measured concentration of the calcium hydroxide after filtration. The iron (II) chloride solution and iron (III) chloride solution are then combined to obtain a "mixed" iron chloride solution.

A phosphoric acid solution was prepared by adding 6.333 g phosphoric acid into 50 ml of water. This was stirred to combine and dissolve the phosphoric acid in the water. 1% wt/v of chitosan was then added to the phosphoric acid solution and stirred until no large chunks remained. This solution was then filtered using a 5 μm syringe filter and then filtered again using a 0.45 μm syringe filter providing a phosphoric acid/chitosan solution.

The calcium hydroxide solution and the "mixed" iron chloride solution were then combined and stirred until homogenous. The pH of the combined solutions was in the 11.5. In addition, the combined solutions were dark brown-black in color. The combined solutions were brought to a temperature in of 40° C. by heating in a water bath while stirring.

The phosphoric acid-chitosan solution was then added dropwise to the combined solutions of the "mixed" iron chlorides and the calcium hydroxide until a pH of 5.00 was obtained. A mixture including iron oxide-calcium phosphate particles, i.e., magnetic calcium phosphate particles, was obtained. The mixture was stirred overnight for 12 hours at room temperature, i.e., approximately 21° C.

A solution of 20 ml of 0.5% chitosan in 1% acetic acid was prepared and added to the mixture including the magnetic calcium phosphate particles while stirring. The combined acetic acid-chitosan solution and mixture were heated to 40° C. and aged overnight for 12 hours. The combined acetic acid-chitosan solution and mixture were then removed from heat and aged overnight for 12 hours while stirring. The solution was then sonicated for 30 minutes reducing the particle size.

Figure 6:
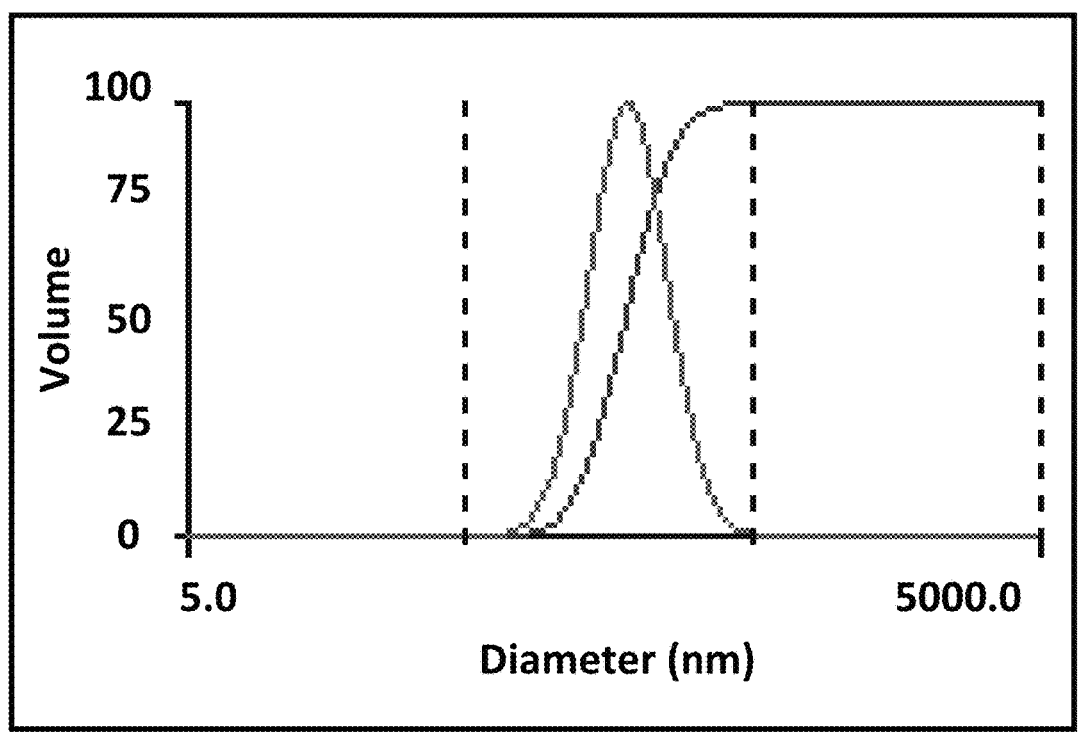
FIG. 6 illustrates the measured effective particle diameter of a sample of magnetic calcium phosphate nanoparticles.
Figure 7:
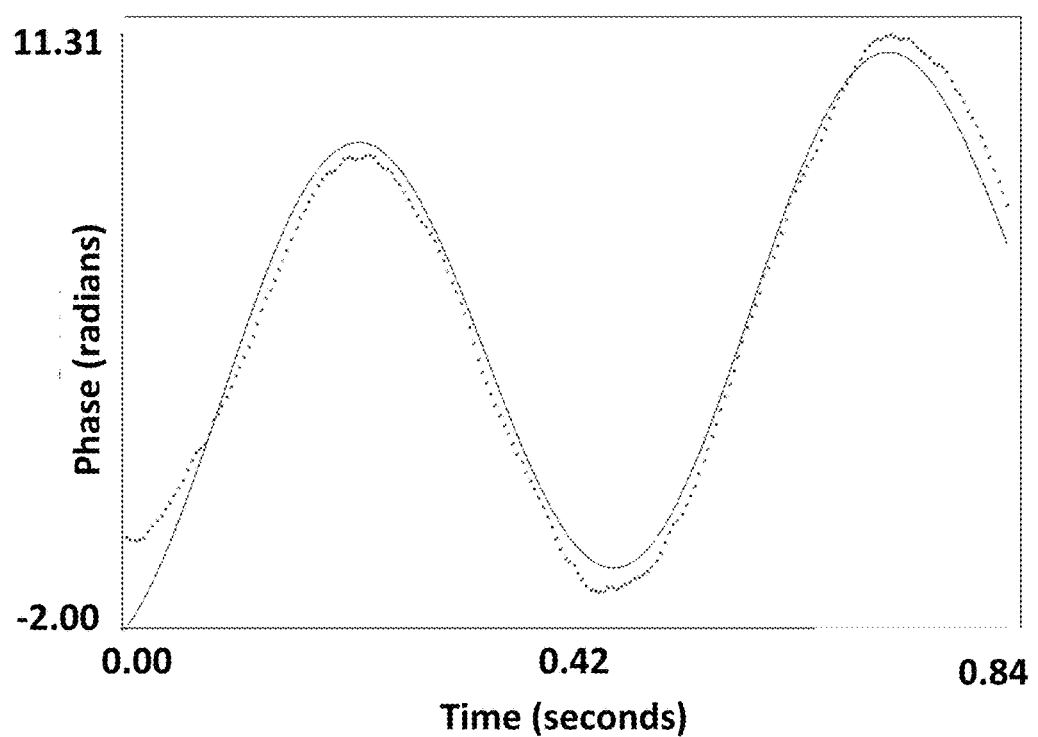
FIG. 7 illustrates the zeta potential measurement of the magnetic calcium phosphate nanoparticles.

The resulting particles exhibited an effective diameter of 228 nm and a polydispersity of 0.120 as illustrated in FIG. 6 and Table 1 below. In addition, as illustrated in FIG. 7 and described in Table 2 below, the resulting particles exhibited a zeta potential of approximately 50 mVolts. The measurement parameters include a conductance of 172 μS, an electric field of 7.17 V/cm and a sample count rate of 737 kcps, whereas the reference count rate was 1800 kcps.

TABLE 1

Effective Diameter and Polydispersity

| Run | Eff. Diameter (nm) | Half Width (nm) | Polydispersity | Baseline Index |
|---|---|---|---|---|
| 1 | 227.7 | 79.5 | 0.122 | 9.6 |
| 2 | 228.7 | 67.9 | 0.088 | 8.1 |
| 3 | 228.0 | 92.3 | 0.164 | 6.8 |
| Mean | 228.1 | 79.9 | 0.125 | 8.2 |
| Std. Error | 0.3 | 7.1 | 0.22 | 0.8 |
| Combined | 228.4 | 79.3 | 0.120 | 9.7 |

TABLE 2

Measured Zeta Potential

| Run | Mobility | Zeta Potential (mV) | Ref. Residual |
|---|---|---|---|
| 1 | 3.75 | 47.93 | 0.0200 |
| 2 | 3.72 | 47.63 | 0.0166 |
| 3 | 4.08 | 52.19 | 0.0115 |
| 4 | 4.20 | 53.75 | 0.0189 |
| 5 | 3.71 | 47.46 | 0.0149 |
| 6 | 3.78 | 48.34 | 0.0212 |
| 7 | 4.19 | 53.61 | 0.0392 |
| Mean | 3.92 | 50.13 | 0.0203 |
| Std. Error | 0.09 | 1.10 | 0.0034 |
| Combined | 3.92 | 50.12 | 0.0157 |

Example 2

Magnetic calcium phosphate nanoparticles were prepared as follows. A 4.00 L 2.5% w/v calcium hydroxide solution was prepared, mixed and allowed to sit overnight for a period of 12 hours and filtered through a 0.45 μm membrane filter. A 250 ml sample of this solution was drawn. A second solution including 0.213 g of iron (II) chloride hydroxide mixed in 1.25 ml of water and a third solution of 0.300 g of iron (III) chloride hydroxide mixed in 1.25 ml of water were prepared. These two iron solutions were then combined and 0.935 ml were added to the 250 ml sample of the calcium hydroxide solution. The combination of the iron solutions and the calcium hydroxide solution was brought to a temperature of 40° C. in a water bath while stirring.

A fourth solution of 20 ml 1M phosphoric acid w/1% w/v chitosan was prepared. The phosphoric acid-chitosan solution was sequentially filtered through a 5 μm filter and 0.45 μm filter. This solution was then titrated dropwise by hand into the combined solutions of the calcium hydroxide and iron chlorides until a pH of 5.0 was reached. A mixture including particles comprising iron oxide and calcium phosphate was obtained, i.e., magnetic calcium phosphate particles. The mixture was stirred overnight for 12 hours at room temperature, i.e., 21° C.

Figure 8:
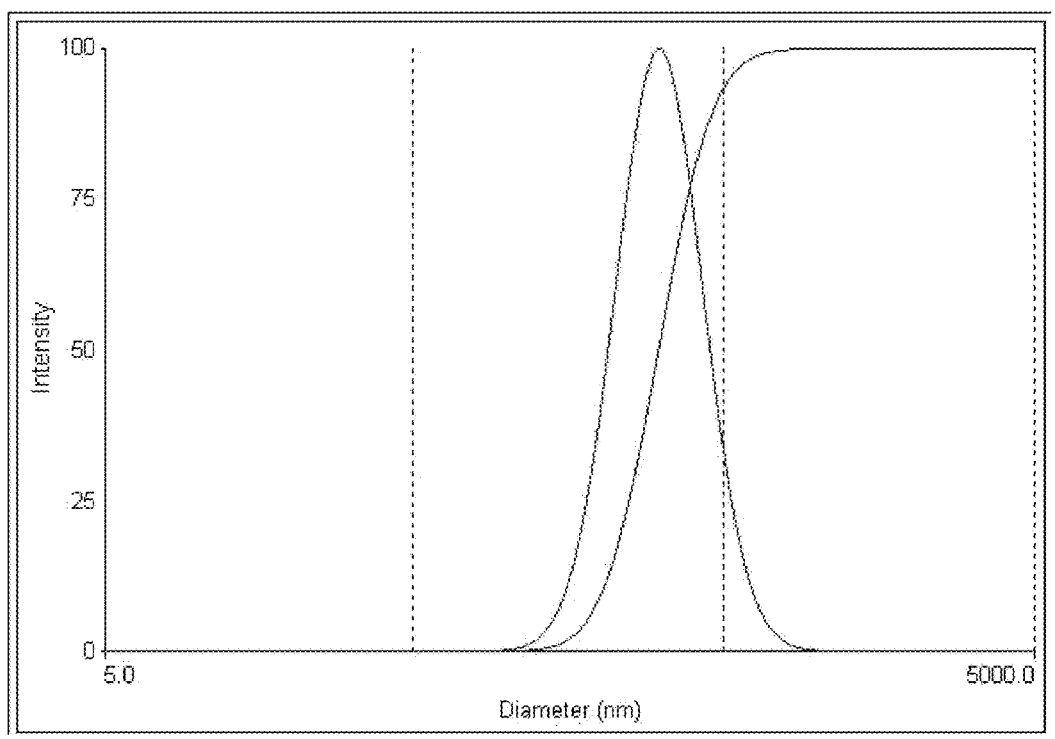
FIG. 8 illustrates the measured effective diameter of another sample of magnetic calcium nanoparticles.
Figure 9:
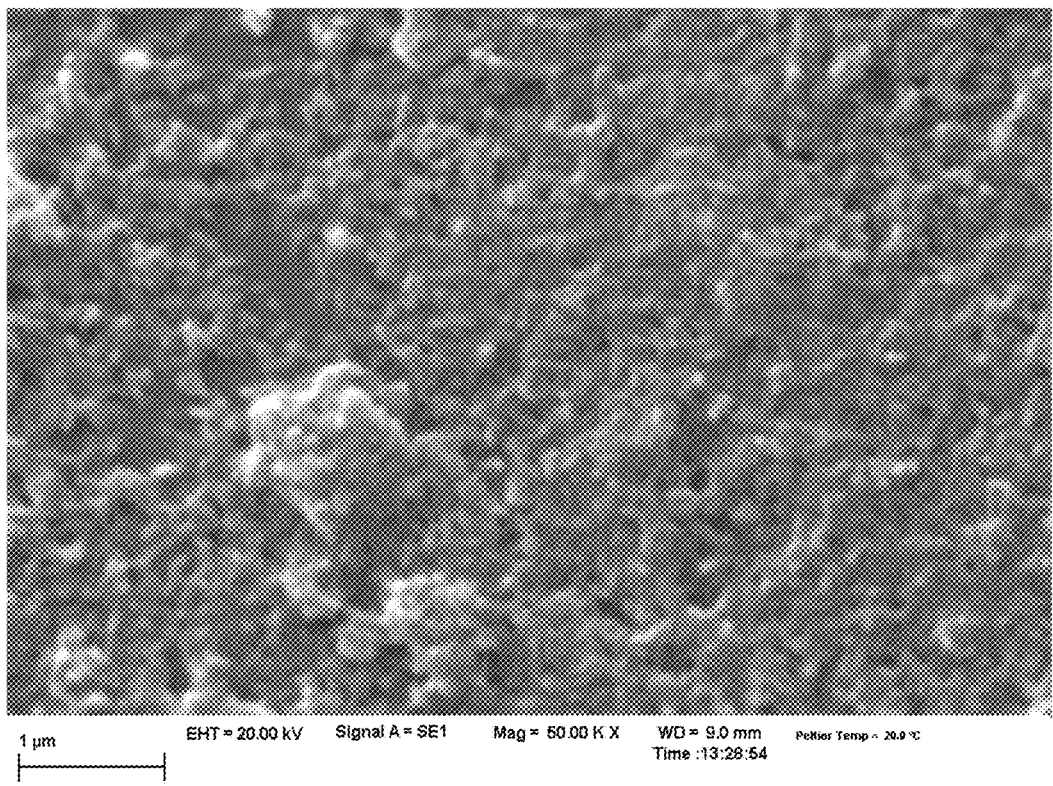
FIG. 9 illustrates an SEM image of the prepared magnetic calcium phosphate nanoparticles at a 1 μm scale taken under 50.00 K magnification.

After aging, 25 ml of the magnetic calcium phosphate particles in suspension were withdrawn and added to a centrifuge tube. 2 mL of 1% acetic acid with 0.5% chitosan was added to the tube and left to age over the weekend for 72 hours at 40° C. The sample was tested for particle size, sonicated and tested for particle size again. After sonication, the particle size was found to be about 300 nm with a polydispersity of 0.110 as illustrated in FIG. 8. FIG. 9 includes an SEM image of the prepared magnetic calcium phosphate nanoparticles at 1 μm scale taken under 50.00 K magnification.

Figure 10A:
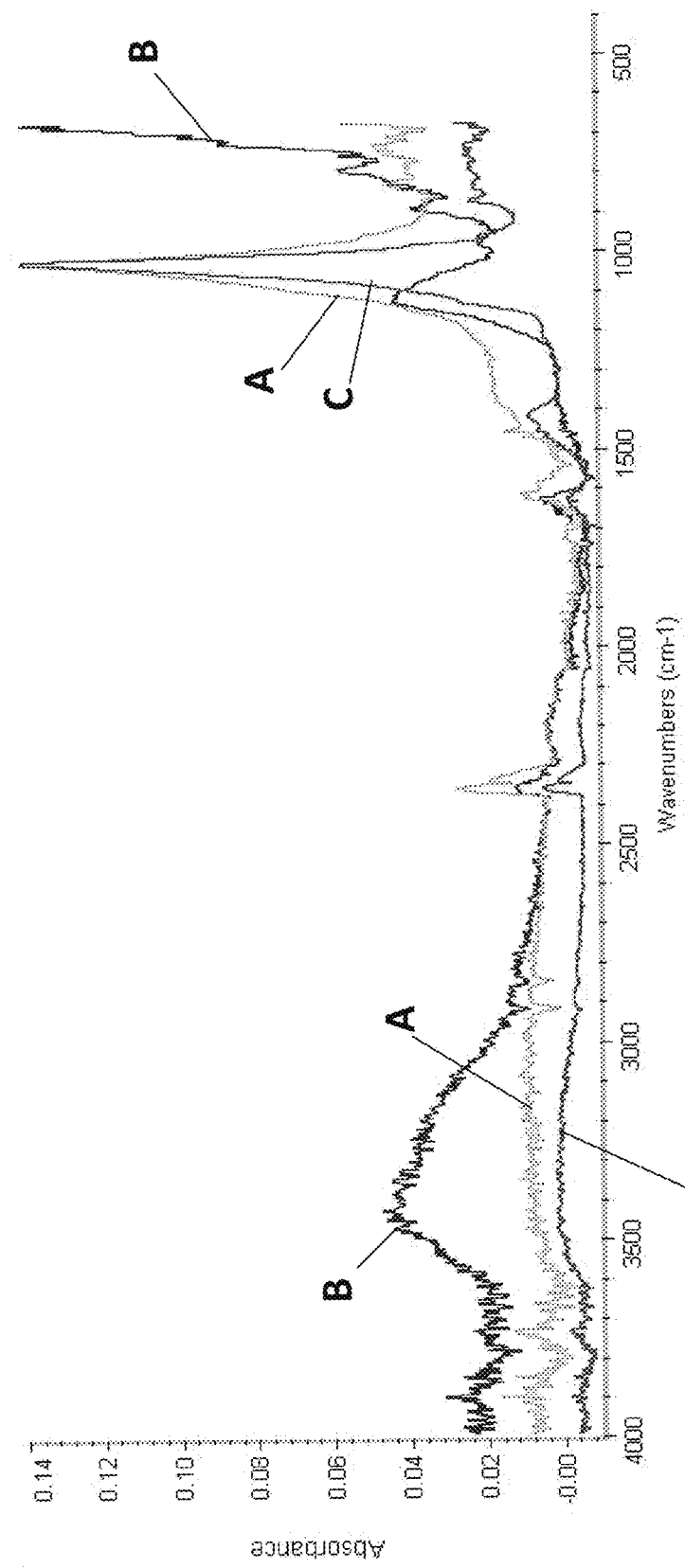
FIGS. 10a and 10b illustrate FTIR spectrums for 1) magnetic calcium phosphate (A) synthesized herein, 2) pure iron oxide particles (B), and 3) pure hydroxyapatite nanoparticles (C)
Figure 10B:
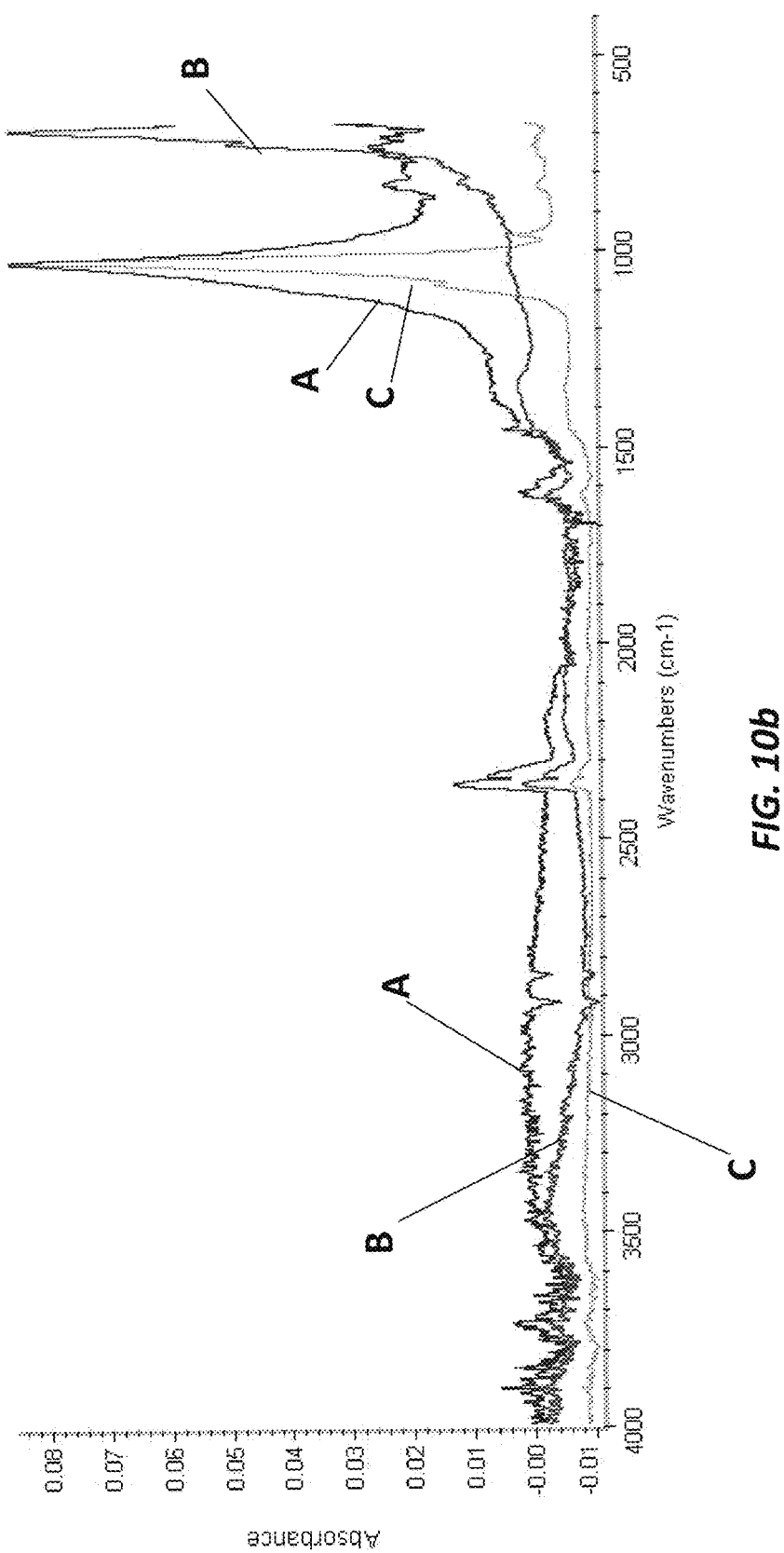

Fourier Transform Infrared Spectroscopy (FTIR) analysis was also performed using three different particles: 1) magnetic calcium phosphate (A) synthesized herein, 2) pure iron oxide particles (B), and 3) pure hydroxyapatite nanoparticles (C). The magnetic calcium phosphate has the characteristic peaks of both the hydroxyapatite nanoparticles and the iron oxide as seen in FIGS. 10a and 10b.

Figure 11:
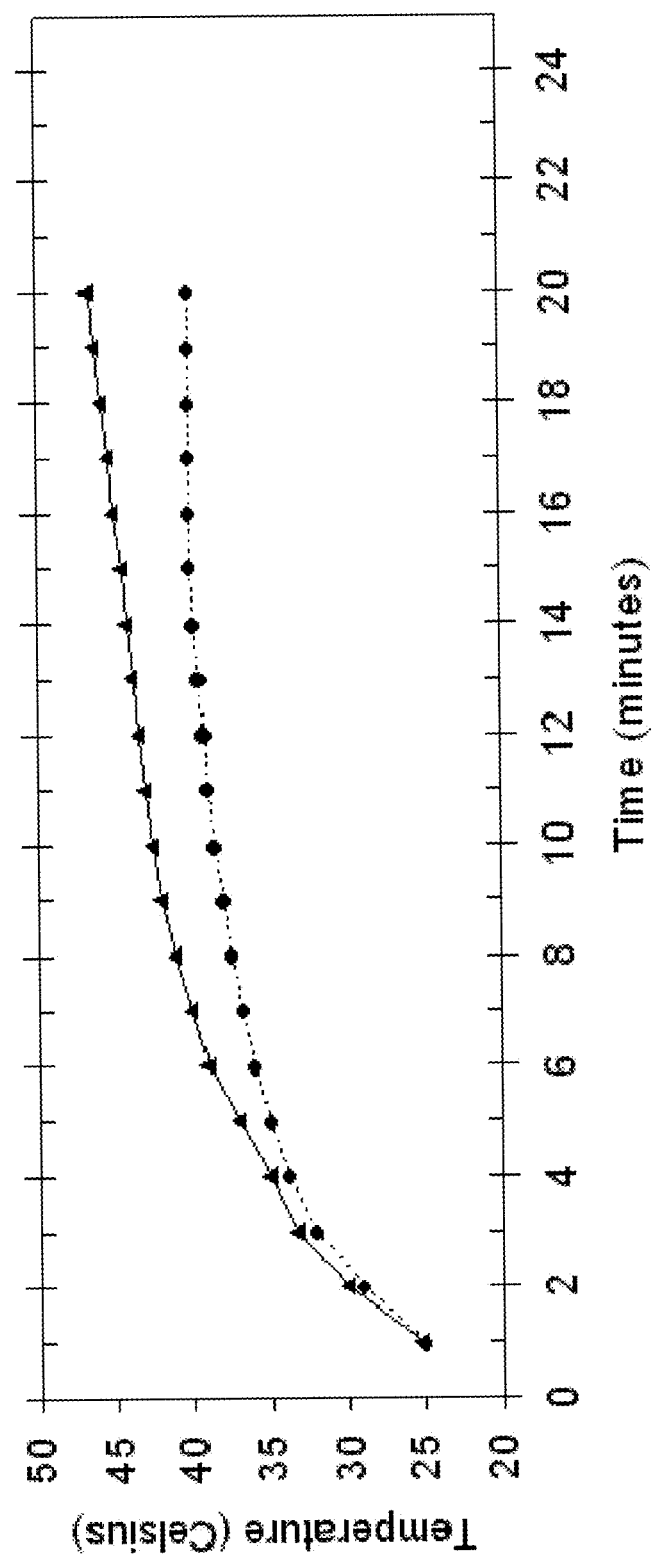
FIG. 11 illustrates the increase temperature over time for 10% by weight and 15% by weight suspensions of the magnetic calcium phosphate particles in water upon application of alternating current through the coil.

Further, suspensions of the magnetic calcium phosphate nanoparticles in water were prepared at levels of 10% by weight and 15% by weight of the particles relative to the total combination of the particles and water. The magnetic calcium phosphate particles were heated under an alternating magnetic field using an IHG061A induction machine at a current of 25 A and at 330 kHz. FIG. 11 illustrates the time to heat the magnetic calcium phosphate particles in a water suspension. As illustrated, the temperature of the water suspension rises to above 40 degrees C. within approximately 15 minutes for the 10% by weight suspension and within 8 minutes for the 15% by weight suspension.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A method of forming a mixture of magnetic iron oxide and calcium phosphate particles, comprising:
    preparing a calcium hydroxide solution in water;
    filtering said calcium hydroxide solution through a filter;
    forming an iron chloride solution comprising a mixture of Fe(II) and Fe(III) in water;
    combining said iron chloride solution with said filtered calcium hydroxide solution so as to form an homogeneous solution of iron chloride and calcium hydroxide; and
    titrating said homogeneous solution of iron chloride and calcium hydroxide with a phosphoric acid solution to a pH of 5 to 7, wherein said phosphoric acid solution includes phosphoric acid dissolved in water and a polysaccharide, and the phosphoric acid solution is filtered prior to titration using a filter having a pore size of having a pore size of 0.45 µm or less; and
    stirring the titrated mixture so as to form a mixture of magnetic iron oxide nanoparticles of the formula $Fe_2O_3$ and $Fe_3O_4$ comprising polysaccharide, and calcium phosphate of the formula $Ca_x(PO_4)_y$, wherein the ratio of x:y is in the range of 1 to 3; and
    combining said mixture of magnetic nanoparticles with a solution of organic acid and chitosan and heating said mixture of magnetic nanoparticles and said solution of organic acid and chitosan to a temperature of 40° C. to 100° C. from 8 to 24 hours to coat the mixture of magnetic nanoparticles, said coated magnetic nanoparticles having an average particle size ranging from 200 nm to 400 nm with a polydispersity ranging from 0.01 to 0.5 and a zeta potential of 1 to 60 mV.

2. The method of claim 1, wherein said forming an iron chloride solution comprises dissolving $FeCl_2.4H_2O$ to form an Fe(II) solution, dissolving $FeCl_3.6H_2O$ to form an Fe(III), and combining said Fe(II) solution with Fe(III) solution.

3. The method of claim 1, wherein said filter for said calcium hydroxide solution exhibits a pore size of 0.45 µm or less.

4. The method of claim 1, further comprising agitating said combined solution of said chitosan and said organic acid and said magnetic nanoparticles.

5. The method of claim 1, further comprising washing said nanoparticles.

6. The method of claim 1, further comprising lyophilizing said nanoparticles.

7. The method of claim 1, wherein said calcium hydroxide solution is elevated to a temperature of 40° C.

8. The method of claim 1, wherein said phosphoric acid solution is added to said combined solutions of iron chloride and calcium hydroxide until the pH of said combined solutions is 5.0.

9. The method of claim 1, wherein said polysaccharide comprises chitosan.

10. The method of claim 1, wherein said organic acid comprises an aliphatic carboxylic acid.

* * * * *